United States Patent [19]

Deeter

[11] 4,039,686

[45] Aug. 2, 1977

[54] MANGE CURE

[76] Inventor: Patricia Deeter, 103 Woodlawn Place, Marion, Ill. 62959

[21] Appl. No.: 684,545

[22] Filed: May 10, 1976

[51] Int. Cl.² ............................................. A61K 31/02
[52] U.S. Cl. .................................................... 424/350
[58] Field of Search ......................................... 424/350

[56] References Cited

U.S. PATENT DOCUMENTS

| 2,324,472 | 7/1943 | Allen et al. ........................... 424/350 |
| 2,425,238 | 8/1947 | Fletcher et al. ...................... 424/350 |
| 2,441,553 | 5/1948 | Britton et al. ......................... 424/83 |

*Primary Examiner*—Sam Rosen
*Attorney, Agent, or Firm*—Gravely, Lieder & Woodruff

[57] ABSTRACT

A method for curing mange in dogs. The method involves the external application of methylene chloride to the affected areas of the animal.

4 Claims, No Drawings

MANGE CURE

BACKGROUND OF THE INVENTION

Mange is a skin disease that affects domestic animals. This disease can sometimes affect man. Mange is marked by eczematous inflammation and loss of hair. This disease is caused by a minute parasite of Sarcoptes, Psoroptes, Chorioptes, or related genera that burrows in or lives on the skin, or of Demodex that lives in the hair follicles or sebaceous glands.

A preparation is disclosed in Kanfoush, U.S. Pat. No. 3,808,319, for treating skin diseases in humans and animals, including mange in dogs with a mixture of benzylbenzoate, benzocaine, isopropyl alcohol, and trichloroethylene. Methylene chloride, used alone or with other ingredients, has been used to kill Coccidia and Ascaridae worm eggs which have solid protective shells. A method for this use of methylene chloride is disclosed in Rohner, U.S. Pat. No. 3,496,271. Fletcher, U.S. Pat. No. 2,425,238 discloses a methylene chloride-ethylene bromide mixture for killing insects, weevils, borers, and beetles.

In advanced cases of mange, conventional cures are often not successful. I have discovered that methylene chloride is effective in treating advanced cases of mange in dogs. I have used methylene chloride by itself, but a diluent can be employed if desired for some purposes.

SUMMARY OF THE INVENTION

This invention is embodied in a method of treating and curing mange in dogs. This method involves the external application of methylene chloride to the affected areas of the animal.

DETAILED DESCRIPTION

The methylene chloride used in the present invention is industrial grade methylene chloride. A suitable industrial grade methylene chloride composition is that produced by Diamond Shamrock Co. This composition is 99.3% pure methylene chloride. The impurities include other chlorinated hydrocarbons and water (from 50 ppm up to 1.5% by weight). This methylene chloride was used to treat and cure mange in dogs.

A suitable applicator, such as a brush, cotton balls or cloth or cotton tipped sticks, is used to spread or apply the methylene chloride directly on the affected areas of the animal. The affected area should be swabbed in this manner with methylene chloride at least once a day. This daily treatment should be carried on until new hair growth can be detected. Care should be exercised so that the methylene chloride does not contact the eyes of the affected animal or the eyes of the one applying the solution.

A dog was treated with full strength methylene chloride until the dog was cured in about 30 days. The dog previously had received treatment by a veterinary over a period of two months' time using the usually accepted treatments, but without curing the mange or partially curing it.

By applying full strength methylene chloride directly to the affected or infected area, the mange was cured in 30 days. The application was by a brush soaked with methylene chloride and dabbed directly on the area until it was moist with methylene chloride. The dog was held until the medication had dried so that it could not physically be removed by the dog, either through licking it off or rolling on the ground.

What is claimed is:
1. A method for treating mange by applying an effective amount of methylene chloride to the affected areas of the patient.
2. The method of claim 1 wherein the methylene chloride is applied externally.
3. The method of claim 1 wherein the methylene chloride is applied from one time to two times per 24 hours.
4. The method of claim 1 wherein the treatment is conducted for about thirty days.